United States Patent
Busolli et al.

(10) Patent No.: US 8,378,103 B2
(45) Date of Patent: Feb. 19, 2013

(54) PROCESS FOR THE PREPARATION OF TIOTROPIUM BROMIDE

(75) Inventors: Jonathan Busolli, Carisio (IT); Nicola Diulgheroff, Turin (IT); Francesca Scarpitta, Ivrea (IT); Roberta Volonte, Rovellasca (IT); Alessandro Pontiroli, S. Maria della Versa (IT)

(73) Assignee: Sicor, Inc., Irvine, CA (US)

( * ) Notice: Subject to any disclaimer, the term of this patent is extended or adjusted under 35 U.S.C. 154(b) by 457 days.

(21) Appl. No.: 12/651,796

(22) Filed: Jan. 4, 2010

(65) Prior Publication Data
US 2010/0105913 A1    Apr. 29, 2010

Related U.S. Application Data

(62) Division of application No. 12/403,984, filed on Mar. 13, 2009, now Pat. No. 7,662,963, and a division of application No. 11/827,443, filed on Jul. 10, 2007, now abandoned.

(60) Provisional application No. 60/836,037, filed on Aug. 7, 2006, provisional application No. 60/835,201, filed on Aug. 3, 2006, provisional application No. 60/835,200, filed on Aug. 3, 2006, provisional application No. 60/830,231, filed on Jul. 10, 2006.

(51) Int. Cl.
*C07D 451/10* (2006.01)

(52) U.S. Cl. ......................................................... 546/91
(58) Field of Classification Search ..................... 546/91
See application file for complete search history.

(56) References Cited

U.S. PATENT DOCUMENTS

| 4,608,377 | A  | 8/1986  | Banholzer et al. |
| 5,610,163 | A  | 3/1997  | Banholzer et al. |
| 6,608,055 | B2 | 8/2003  | Sieger et al. |
| 6,777,423 | B2 | 8/2004  | Banholzer et al. |
| 7,041,674 | B2 | 5/2006  | Breifelder et al. |
| 7,491,824 | B2 | 2/2009  | Lock et al. |
| 2002/0110529 | A1 | 8/2002  | Bechtold-Peters et al. |
| 2004/0242622 | A1 | 12/2004 | Mammen et al. |
| 2005/0096341 | A1 | 5/2005  | Banholzer et al. |
| 2006/0246009 | A1 | 11/2006 | Morissette et al. |

FOREIGN PATENT DOCUMENTS

| GB | 1 469 781 | 4/1977 |
| WO | WO 02/30928 A1 | 4/2002 |
| WO | WO 02/32898 A2 | 4/2002 |
| WO | WO 02/051840 A1 | 7/2002 |
| WO | WO 2005/042527 A1 | 5/2005 |
| WO | WO 2006/117299 A2 | 11/2006 |
| WO | WO 2006/117300 A2 | 11/2006 |
| WO | WO 2009/087419 A1 | 7/2009 |

OTHER PUBLICATIONS

Jingxi Xie et al., "Improvement of Studies on Total Synthesis of Anisodine," Chemical Abstracts Service, Columbus, Ohio, US; AN 1982:616529, XP00242293, Compounds RN 833350-03-02.

Yaping Zhuang and Liqin Zhao, "Systemic Analysis of 150 Kinds of Tablet," Chemical Abstracts Service, Columbus, Ohio, US; AN 1982: 568993, XP002482294, Compounds RN 83350-03-2.

Hans E. Schink, Helena Pettersson and Jan-E Backvall, "Stereocontrolled Epoxidations of Cycloheptene Derivatives in the Palladium-Catalysed Route to Tropane Alkaloids," Journal of Organic Chemistry, vol. 56, No. 8, 1991, pp. 2769-2774, XP002482292, Scheme II, p. 2770; 2nd Full Par. p. 2771; Scopine Hydrochloride (1 .HC1) p. 2773.

Teva Pharmaceutical Industries, "Tiotropium Bromide Form V", Publication No. IPCOM000143595D, Nov. 2006.

*Primary Examiner* — Patricia Morris
(74) *Attorney, Agent, or Firm* — Arent Fox LLP

(57) ABSTRACT

The invention is directed to improved processes for preparing Tiotropium bromide.

4 Claims, No Drawings

PROCESS FOR THE PREPARATION OF TIOTROPIUM BROMIDE

CROSS REFERENCE TO RELATED APPLICATIONS

This application is a divisional of U.S. patent application Ser. No. 12/403,984, filed Mar. 13, 2009, which is a divisional of U.S. patent application Ser. No. 11/827,443, filed Jul. 10, 2007, which, in turn, claims the benefit of the filing date of U.S. Provisional Patent Application No. 60/830,231 filed Jul. 10, 2006; U.S. Provisional Patent Application No. 60/835,201, filed Aug. 3, 2006; U.S. Provisional Application No. 60/835,200, filed Aug. 3, 2006; and U.S. Provisional Application No. 60/836,037, filed Aug. 7, 2006, the disclosures of which are hereby incorporated herein by reference. This application is also related to U.S. patent application Ser. No. 11/643,013, filed Dec. 19, 2006.

FIELD OF THE INVENTION

The invention is directed to improved processes for preparing Tiotropium bromide.

BACKGROUND

Tiotropium bromide, (1β,2β,4β,5α,7β)-7-[(hydroxydi-2-thienylacetyl)oxy]-9,9-dimethyl-3-oxa-9-azoniatricyclo[3.3.1.0]nonane bromide or 6β,7β-epoxy-3β-hydroxy-8-methyl-1αH,5αH-tropanium bromide, di-2-thienylglycolate, has the following chemical structure:

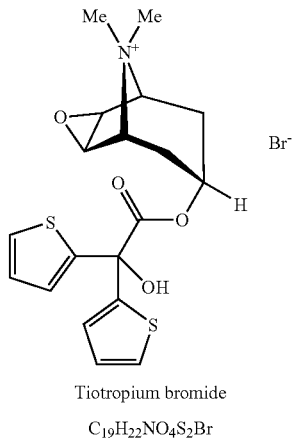

Tiotropium bromide $C_{19}H_{22}NO_4S_2Br$

It is an anticholinergic drug with specificity for muscarinic receptors. As a bronchodilator it provides therapeutic benefit in the treatment of asthma or chronic obstructive pulmonary disease (COPD). This active pharmaceutical ingredient is administered by inhalation, and is available commercially as SPIRIVA® HandiHaler®.

Tiotropium bromide was first disclosed in U.S. Pat. No. 5,610,163 where it was synthesized via N-demethyl tiotropium of formula III,

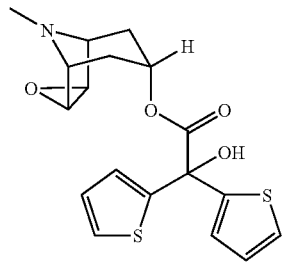

which was obtained by a reaction of methyl di(2-thienyl) glycolate of formula I and Scopine of formula II using sodium metal in melt or sodium methoxide in melt. Because of the dangerous reaction conditions, this method is not suitable for industrial scale preparation. The quaternization of N-demethyl-tiotropium is then carried out in a mixture of acetonitrile and methylene chloride using methyl bromide as a quaternizing agent. The process is illustrated in the following scheme:

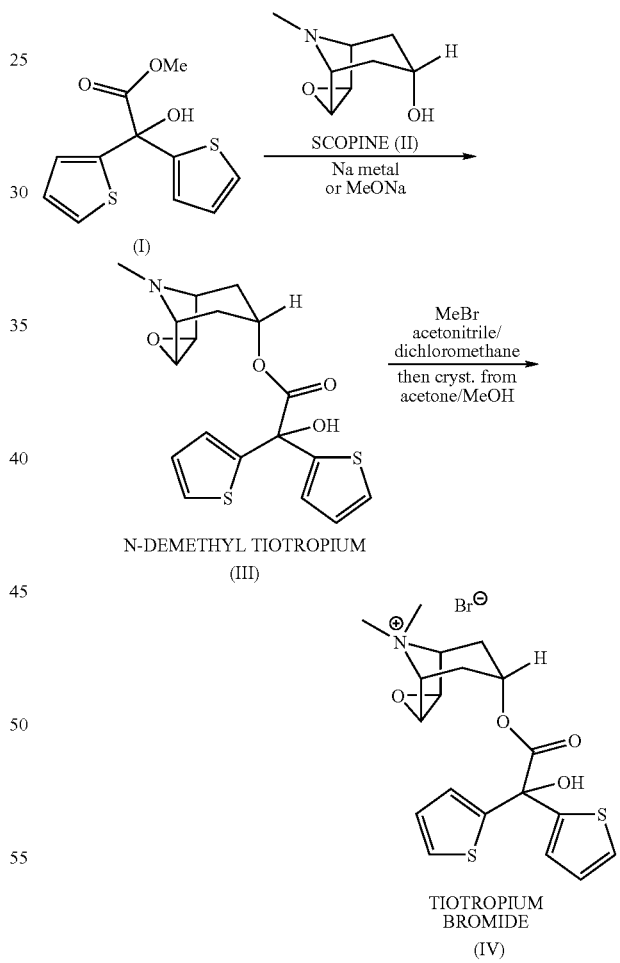

The product was then crystallized from a mixture of acetone and methanol.

Also described in the prior art is the preparation of Scopine HCl, which was first disclosed in GB 1469781, wherein it was prepared by reduction of scopolamine using sodium borohydride, followed by addition of HCl to the reaction mixture, a process illustrated by the following scheme:

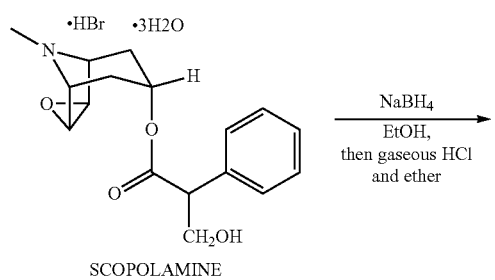

SCOPOLAMINE

NaBH₄
EtOH,
then gaseous HCl
and ether

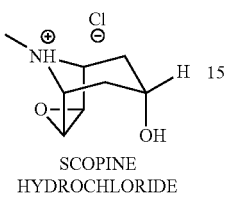

SCOPINE
HYDROCHLORIDE

This salt of scopine can be used as a precursor for scopine base, however a process to remove inorganic salts from the desired product is not reported.

U.S. Pat. Nos. 6,486,321 and 6,506,900 disclose a synthesis of Tiotropium and analogues via tropenol derivatives by introducing an additional epoxidation step, as described by the following scheme.

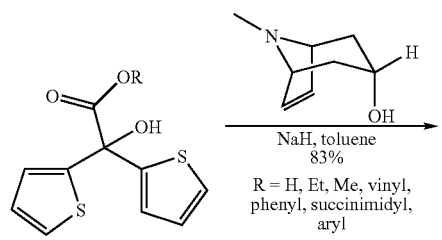

NaH, toluene
83%

R = H, Et, Me, vinyl,
phenyl, succinimidyl,
aryl

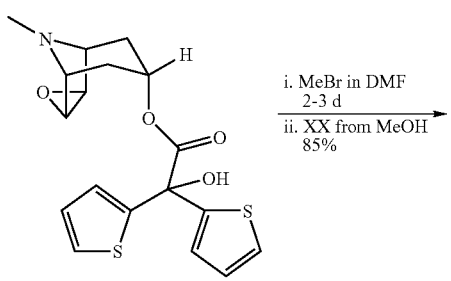

V₂O₅, H₂O₂
DMF

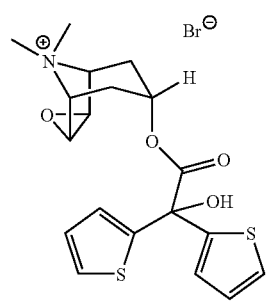

Tiotropium Bromide

U.S. Pat. No. 6,747,154, refers to formal approaches by stating "These processes known in the art may also be used to prepare the compounds of formula I.

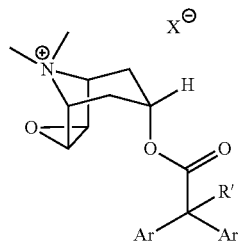

However, these methods of synthesis are more complex procedures involving a number of synthetic steps." Therefore a different synthetic approach was developed, where the coupling is carried out using scopine methobromide rather than scopine, but details, including the yield, of this coupling reaction are not reported.

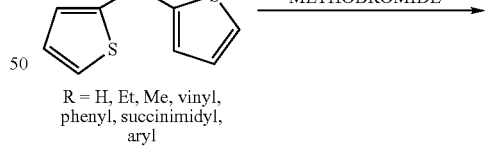

R = H, Et, Me, vinyl,
phenyl, succinimidyl,
aryl

SCOPINE
METHOBROMIDE i. MeBr in DMF
2-3 d
ii. XX from MeOH
85%

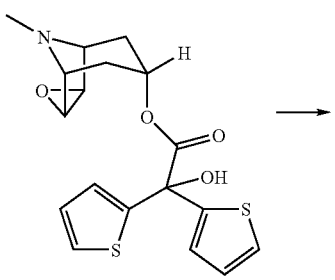

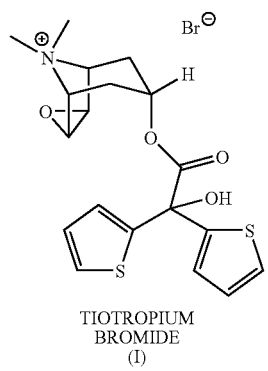

TIOTROPIUM
BROMIDE
(I)

United States Patent Publication No 2006/0047120 describes yet another approach, coupling scopine methobromide with trimethylsilyl-protected sodium dithienyl glycolate which is obtained in situ.

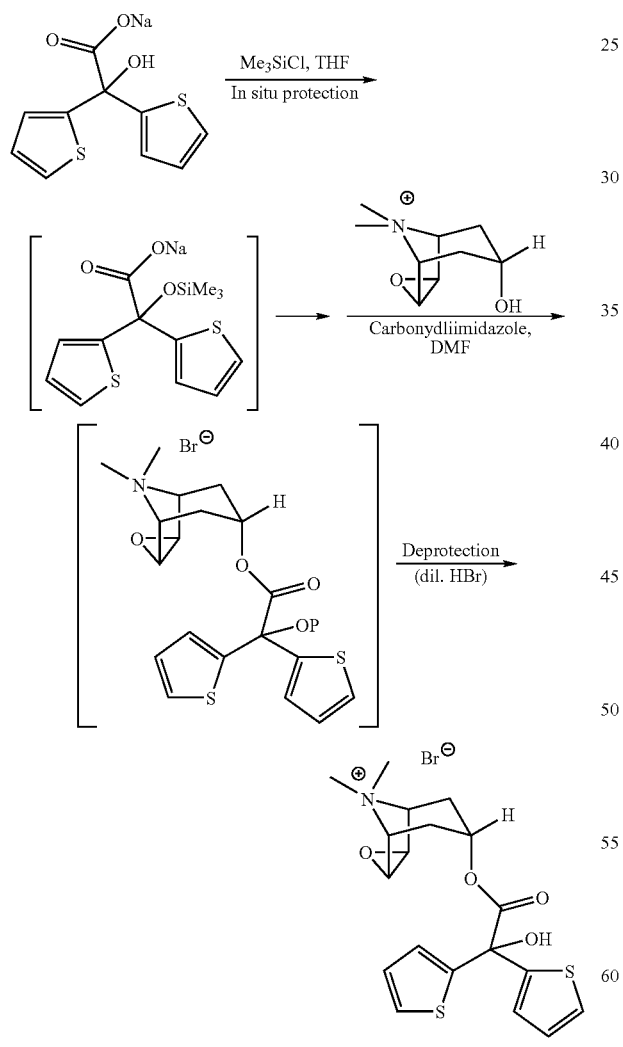

This application, provides that this approach was developed to improve the prior art synthesis for Tiotropium bromide.

Hence, an improved process to prepare Tiotropium bromide is needed.

SUMMARY OF THE INVENTION

In one embodiment, the present invention encompasses scopine salt of formula II-s:

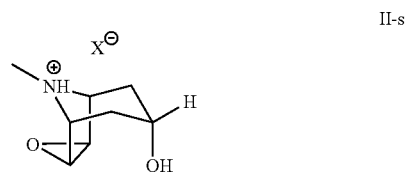

containing about 0.5% to about 40% by weight of salts; wherein X is Br, $C_1$, $SO_4$, MeCOO, $PO_4$, $MeSO_3$, tartrate, fumarate, citrate, maleate, succinate, p-toluene sulphonate or amidosulphonate.

In another embodiment, the present invention encompasses a process to convert scopine salt of formula II-s containing about 0.5% to about 40% by weight of salts to Tiotropium bromide of formula IV.

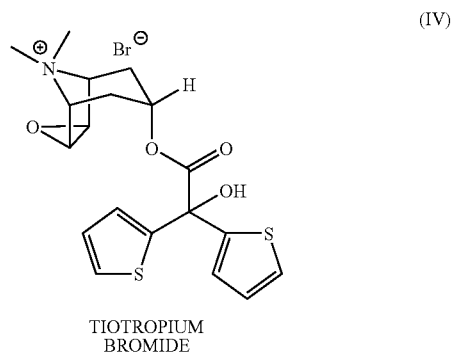 [SMILES: C[N+]1(C)C2CC(OC(=O)C(O)(c3cccs3)c3cccs3)CC1C1OC12 ; Br]

TIOTROPIUM
BROMIDE

In yet another embodiment, the present invention encompasses the preparation of N-demethyl-tiotropium of formula III,

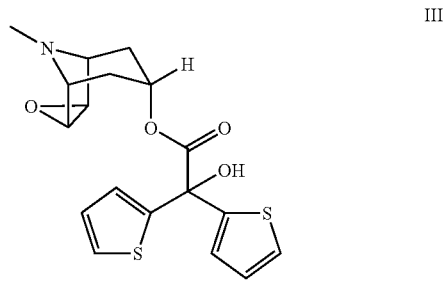 [SMILES: CN1C2CC(OC(=O)C(O)(c3cccs3)c3cccs3)CC1C1OC12]

comprising combining methyl-di-(2-thienyl)-glycolate of formula I,

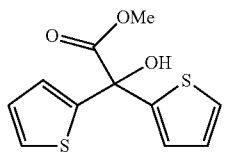

a weak inorganic base, a polar organic solvent and scopine salt of formula II-s

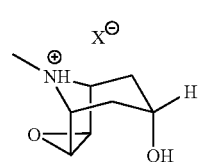

containing about 0.5% to about 40% by weight of salts to obtain a mixture, and heating the mixture.

In one embodiment, the present invention encompasses a process for the preparation of Tiotropium bromide comprising a) combining methyl-di-(2-thienyl)-glycolate of formula I,

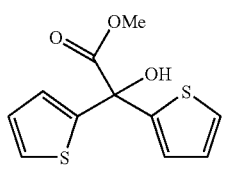

a weak base, a polar organic solvent, and scopine salt of formula II-s containing about 0.5% to about 40% by weight of salt to obtain a mixture; b) heating the mixture providing N-demethyl-tiotropium of formula III; c) recovering the N-demethyl-tiotropium of formula III; d) combining N-demethyl-tiotropium of formula III with methylbromide (MeBr) and an organic solvent to yield Tiotropium bromide.

In another embodiment, the present invention encompasses a process to prepare Tiotropium bromide, by preparing N-demethyl-tiotropium of formula III by the process of the present invention, and further converting it to Tiotropium bromide.

DETAILED DESCRIPTION OF THE INVENTION

As used herein, the term "room temperature" refers to a temperature ranging from about 20° C. to about 26° C.

The present application discloses a novel approach to the synthesis of Tiotropium bromide, in particular from a Scopine hydrohalide of formula II-s, and even more specifically, from scopine HBr of the formula

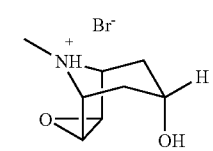

that contains a low level of salts, as compared to the process disclosed in GB '781, where the obtained scopine HCl contained a high level of more than 60% by weight of inorganic salts. These salts are insoluble in water, and thus cannot be removed by a simple washing operation.

Typically, scopine hydrohalide containing low level of salts refers to scopine salt with less than 40% by weight of salts. Typically, the measurement of the salts content is done by sulfuric ashes, as exemplified in example 1.

Moreover, the inventors of this application have found that the purity of the scopine salt affects the purity and the yield of N-demethyl-tiotropium of formula III, a key intermediate in the synthesis of Tiotropium bromide.

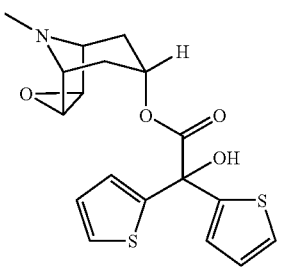

For example, without restricting the invention, using pure scopine salt leads to higher yield and purity, as will be further demonstrated.

The present invention encompasses scopine salt of formula II-s

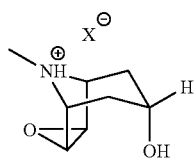

containing about 0.5% to about 40% by weight of salts; wherein X is Br, $C_1$, $SO_4$, MeCOO, $PO_4$, $MeSO_3$, tartrate, fumarate, citrate, maleate, succinate, p-toluene sulphonate or amidosulphonate.

Preferably, scopine salt of formula II-s contains about 0.5% to about 20% by weight of salts, more preferably of about 0.5% to about 15% by weight, even more preferably of about 0.5% to about 5% by weight, and most preferably of about 0.5% to about 1% by weight. As mentioned before, the content of the salts can be determined by sulfuric ashes.

Preferably, the scopine salt is selected from a group consisting of HBr, HCl, $H_2SO_4$, $CH_3COOH$, $H_3PO_4$, $MeSO_3H$, tartrate, fumarate, citrate, maleate, succinate, maliate, p-toluenesulphonate, and amidosulphonate. More, preferably, the salt is HBr.

The above scopine salt of formula II-s is obtained by filtration of the reaction mixture prior to the addition of acid. The process comprises: a) filtering solids from the reaction mixture containing scopine base and insoluble inorganic salts, such as borate salts, to produce a filtrate; b) washing the solids with a polar organic solvent; c) adding water to the filtrate to precipitate insoluble inorganic salts; d) filtering the filtrate to remove any precipitated salts; e) washing the inorganic salts with a polar organic solvent; and f) adding an acid and a polar organic solvent to the filtrate to obtain the scopine salt of formula II-s.

The addition of water in the above process causes the remaining insoluble salts to precipitate. Preferably, after the addition of water the filtrate is stirred for about 0.5 hour to about 2 hours, more preferably for about 1 to about 1.5 hours.

Typically, the addition of water results in a precipitate formation and thus a suspension. The suspension is concentrated under vacuum, to remove water, thus increasing the yield. Preferably, the suspension is concentrated at a temperature of no more than 55° C., more preferably of about 25° C. to about 55° C., most preferably of about 30° C. to about 35° C.

After the suspension is concentrated, it is filtered, and washed twice with a polar organic solvent. Preferably, the polar organic solvent is selected from a group consisting of $C_{1-6}$ alcohol, $C_{4-8}$ ether, $C_{3-10}$ ketone, $C_{2-4}$ nitrile, and mixtures thereof. Preferably, the $C_{1-6}$ alcohol is $C_{1-4}$ alcohol, more preferably $C_{1-3}$ alcohol. Preferably, the $C_{1-3}$ alcohol is methanol, ethanol or isopropanol. Moreover, absolute ethanol may be used. A preferred $C_{4-8}$ ether is $C_{4-6}$ ether, more preferably $C_{4-6}$ ether. A preferred $C_{4-5}$ ether is either tetrahydrofuran or 1,4-dioxane. Preferably, the $C_{3-10}$ ketone is $C_{2-3}$ ketone. Preferably, the $C_{2-3}$ ketones acetone. A preferred $C_{2-4}$ nitrile is $C_{1-2}$ nitrile. Preferably, the $C_{1-2}$ nitrile is acetonitrile. Most preferably, the solvent is ethanol.

Preferably, the acid is HBr.

The obtained scopine salt of formula II-s is then converted to Tiotropium bromide of formula IV. The conversion will be illustrated below.

The novel approach, also comprises a process for the preparation of Tiotropium bromide comprising: a) combining methyl-di-(2-thienyl)-glycolate of formula I,

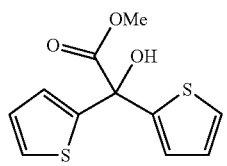
I a weak inorganic base, a polar organic solvent, and scopine salt of formula II-s containing about 0.5% to about 40% by weight of salt to obtain a mixture; b) heating the mixture providing N-demethyl-tiotropium of formula III; c) recovering the N-demethyl-tiotropium of formula III; d) combining N-demethyl-tiotropium of formula III with methylbromide (MeBr) and an organic solvent to yield Tiotropium bromide.

The process is illustrated by the following scheme:

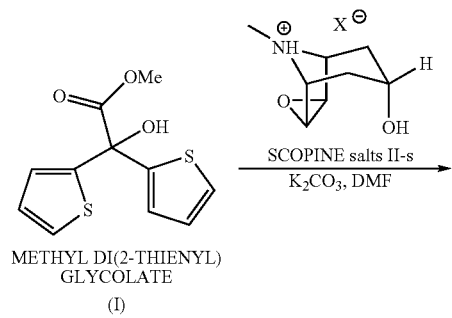
METHYL DI(2-THIENYL) GLYCOLATE
(I)

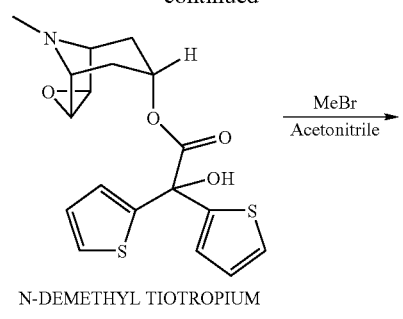
N-DEMETHYL TIOTROPIUM
(III)

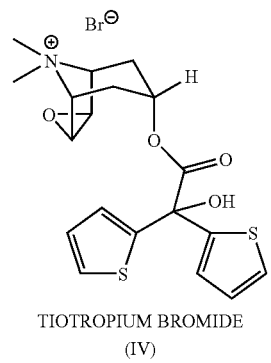
TIOTROPIUM BROMIDE
(IV)

wherein X is Br, $C_1$, $SO_4$, MeCOO, $PO_4$, $MeSO_3$, tartrate, fumarate, citrate, maleate, succinate, p-toluene sulphonate or amidosulphonate.

The glycolate of formula I may be prepared by combining 2-bromo-thiophene of the following formula,

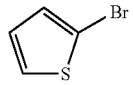

Mg, and an ethereal solvent; combining with dimethyloxalate of the following formula

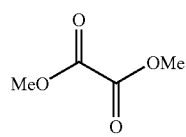

and quenching.

Combining 2-bromo-thiophene, Mg, and an ethereal solvent provides a Grignard reagent that can be prepared, for example, according to the process disclosed in Nyberg, K. Acta Chemica Scandinavica, 24, 1970, 1590-1596.

Methyl di-(2-thienyl)glycolate of formula I may be purified by crystallization from a mixture of ethanol and heptane, absolute ethanol and heptane, isopropanol and heptane, and from toluene and heptane.

N-demethyl-tiotropium of formula III

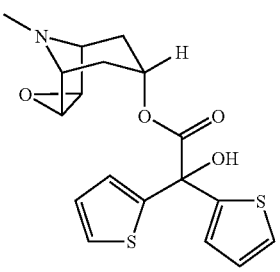

is prepared under conditions, which are not dangerous, are suitable for industrial scale preparation, and which provide a satisfactory yield. Moreover, the use of scopine salt instead of scopine base, and applying mild conditions in the preparation of N-demethyl-tiotropium of formula III, decrease significantly the conversion of scopine to scopoline, a side product that occurs in basic media, as illustrated in the following scheme:

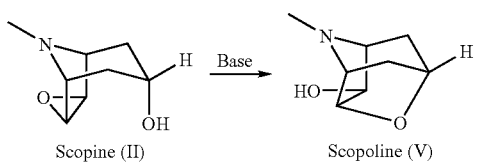

The preparation of N-demethyl-tiotropium of formula III

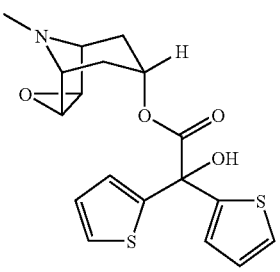

comprises combining methyl-di-(2-thienyl)-glycolate of formula I,

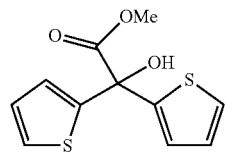

a weak inorganic base, a polar organic solvent, and scopine salt of formula II-s, containing about 0.5% to about 40% by weight of salts to obtain a mixture, and heating the mixture.

Initially, scopine salt of formula II-s is suspended in a polar organic solvent. Preferably, the salt is an HBr salt. The polar organic solvent is selected from a group consisting of amides, sulfoxides, sulfones, aromatic hydrocarbons, nitriles, and mixtures thereof. Preferably, the polar organic solvent is selected from the group consisting of $C_1$-$C_4$ amide, $C_2$-$C_4$ sulfoxide, $C_2$-$C_4$ sulfones, $C_7$-$C_8$ aromatic hydrocarbon, and $C_2$-$C_4$ nitrile. A preferred $C_1$-$C_4$ amide is dimethylformamide, N-methyl-2-pyrrolidone, or dimethylacetamide. A preferred $C_2$-$C_4$ sulfoxide is dimethylsulfoxide. Preferably, the $C_2$-$C_4$ sulfone is sulfolane. Preferably, the $C_2$-$C_4$ nitrile is acetonitrile. Preferably, the $C_7$-$C_8$ aromatic hydrocarbon is toluene. More preferably, the polar organic solvent is dimethylformamide.

Then, the weak inorganic base is added to the suspension providing a new suspension. Typically, an anhydrous weak inorganic base, i.e. having <0.5% of water by weight, is used in such reactions to obtain the free base form of scopine. Preferably, the weak inorganic base has a pKa of about 8 to about 12, even more preferably of about 9 to about 10. Preferably, the weak inorganic base is selected from a group consisting of: $K_2CO_3$, $NaHCO_3$, $Na_2CO_3$, $Li_2CO_3$, $Cs_2CO_3$, t-ButOK, and t-ButOLi. More preferably, the weak inorganic base is $K_2CO_3$.

After the addition of the base, a mixture of Methyl-di-(2-thienyl)-glycolate of formula I and another portion of the weak inorganic base are added to the new suspension, providing the mixture.

Methyl-di-(2-thienyl)-glycolate of formula I can be added as solid or in solution. Preferably, methyl-di-(2-thienyl)-glycolate of formula I is in solution in the polar organic solvent.

Preferably, the weak inorganic base is present in the mixture in an amount of about 0.45 to about 2.5, more preferably, of about 2 to about 2.5 mole equivalent per mole equivalent of scopine salt of formula II-s. The weak inorganic base is added in two portions to prevent decomposition of scopine and to provide favorable reaction conditions.

Preferably, the mixture of the weak inorganic base and methyl-di-(2-thienyl)-glycolate of formula I are added at a temperature of about 25° C. to about 65° C., more preferably at about 60° C. to about 65° C.

Typically, the said mixture is heated in order to provide N-demethyl-tiotropium of formula III. Preferably, the said mixture is heated to a temperature of below 70° C., more preferably, of about 25° C. to about 65° C., even more preferably of about 60° C. to about 65° C., and most preferably of about 63° C. to about 65° C. Preferably, heating is done for about 17 to about 24 hours, more preferably for about 18 to about 20 hours.

Preferably, heating is done under reduced pressure. Usually, the term "reduced pressure" refers to a pressure of about 70 to about 100 millibar.

Usually, such reactions are done under inert conditions, such as under an atmosphere of nitrogen. Inert conditions are provided by bubbling an inert gas, such as nitrogen and/or argon, during the reaction, through a second inlet. Preferably, nitrogen is bubbled in a rate of about 1.8 to about 2.6 L/min, more preferably, of about 2.0 to about 2.4 L/min, and even more preferably of about 2.2 to about 2.4 L/min.

The heating under reduced pressure, while bubbling nitrogen from a second inlet, assists in evaporating methanol, which is formed during the reaction, hence, shifting the reaction towards the formation of the product.

N-demethyl-tiotropium of formula III may be recovered by cooling the mixture; adding an acid to the cooled mixture providing a two phase system comprising of an organic and aqueous phases; extracting the aqueous phase with an organic solvent; adding a base to the aqueous phase to precipitate N-demethyl-tiotropium of formula III; filtering the precipitate N-demethyl-tiotropium of formula III; washing and drying the N-demethyl-tiotropium. Preferably, the acid is HBr.

Preferably, the heated mixture is cooled to a temperature of about 10° C. to about −10° C., more preferably to about 5° C. to about 0° C.

Preferably, the addition of the acid provides a pH of about 2 to about 3.5. Preferably, the organic solvent is toluene.

Preferably, the weak inorganic base is added at a temperature of about 0° C. to about 5° C. Preferably, the weak inorganic base is selected from a group consisting of: $K_2CO_3$, $NaHCO_3$, $Na_2CO_3$, $Li_2CO_3$, $Cs_2CO_3$, t-ButOK, and t-ButOLi. Preferably, the weak inorganic base is $K_2CO_3$.

Preferably, the precipitate is washed with water to obtain pH of about 7.

Optionally, scopine base may be used instead of scopine salt. When scopine base is used, typically, a smaller amount of the weak inorganic base is required. Preferably, about 1 to 1.5 mole equivalent of weak inorganic base per mole equivalent of scopine base may be used.

The obtained N-demethyl-tiotropium of formula III may then be converted to Tiotropium bromide. The conversion can be done, for example, by the process disclosed in U.S. Pat. No. 5,610,163 or by the process of the present invention described below.

The conversion of N-demethyl-tiotropium of formula III to Tiotropium bromide can be done by reacting N-demethyl-tiotropium of formula III with methyl bromide in an organic solvent.

Initially, N-demethyl-tiotropium of formula III and the organic solvent are combined to obtain a suspension. Preferably, the organic solvent is selected from a group consisting of $C_{2-4}$ nitrile, $C_{4-8}$ linear or cyclic ether, mixtures of $C_{2-4}$ nitrile and $C_{4-8}$ linear or cyclic ether, mixtures of $C_{7-8}$ aromatic hydrocarbon and $C_{2-4}$ nitrile, and mixtures of $C_{2-4}$ nitrile and $C_{3-10}$ ketone. Preferably, the $C_{2-4}$ nitrile is acetonitrile. A preferred $C_{4-8}$ linear or cyclic ether is tetrahydrofuran. Preferably, a mixture of $C_{2-4}$ nitrile and $C_{4-8}$ linear or cyclic ether is that of acetonitrile and tetrahydrofuran. A preferred mixture of $C_{7-8}$ aromatic hydrocarbon and $C_{2-4}$ nitrile is that of toluene and acetonitrile. Preferably, a mixture of $C_{2-4}$ nitrile and $C_{3-10}$ ketone is that of acetone and acetonitrile. Most preferably, the solvent is acetonitrile.

Methyl bromide is then added to the suspension to provide a mixture. Methyl bromide can be used as a gas or in solution. Preferably, methyl bromide is used in solution, where the solvent is an organic solvent that is described above.

The mixture is the maintained at a temperature of about 20° C. to about 40° C. Preferably, the mixture is the maintained at a temperature of about 20° C. to about 25° C.

Typically, the mixture is maintained to allow the formation of Tiotropium bromide. Preferably, the mixture is maintained for about 12 to about 64 hours, more preferably for about 18 to about 22 hours.

Tiotropium bromide may then be recovered by any method known in the art, such as filtering and drying. Tiotropium bromide may then be purified by crystallization from ethanol. Preferably, crude Tiotropium bromide is dissolved in ethanol. More preferably, the ethanol is absolute ethanol. Preferably, the dissolution is done by heating to a temperature of about 75 to about 78° C. Typically, after dissolution, the solution is cooled to a temperature of about to about 25° C. to induce precipitation of Tiotropium bromide. Preferably, cooling is done over a period of about 6 to about 8 hours.

The precipitate is recovered from the suspension by filtration, washed with absolute ethanol, and dried.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Sulfuric ashes methodology for determining the level of salts in scopine HBr:

1 g (exactly weighed) of scopine HBr was placed in a platinum melting pot. Sulphuric acid 96% was added, and then placed in an oven at 600° C. until a constant weight was achieved. The melting pot, with the inorganic residue inside, was weighed to afford the percent of inorganic salts present in the original material.

Example 1

Comparative Example

Preparation of Scopine Hydrochloride According to GB '781

10.0 g (22.84 mmol) of scopolamine hydrobromide trihydrate was suspended in 100 mL of absolute ethanol, and cooled to about 0° C. Sodium borohydride (4.0 g, 105.7 mmol) was then added portion-wise while maintaining the temperature at a maximum of 30° C. 4.8 mL of water was then added to the reaction mixture. After 3.5 hours, the reaction was completed and 50 mL of diethyl ether was then added. The reaction was then cooled to 0° C., and acidified with 2M hydrochloric acid in diethyl ether to a pH of about 2. The suspension was stirred at room temperature for 30 minutes and then filtered on GochP3. The white solid was dried at 45° C. under vacuum for 4 hours, yielding 9 g of product containing 79% of salts determined by sulphuric ashes.

Example 2

Preparation of Methyl di-(2-thienyl)glycolate 1050 mL of tetrahydrofuran was loaded in a 2 L round bottomed flask. 22.6 g (0.93 mol) of magnesium turnings were then added, and the mixture was kept at 35° C., while catalytic bromoethane (200 mg, 1.84 mmol) was loaded. 150 g (0.92 mol) of 2-bromothiophene was added dropwise, and after about 15% (13 ml) of reagent was exothermicity was observed. The temperature was maintained at a maximum of 50-55° C., and the remaining 2-bromothiophene was then added. At the end of the addition, the reaction mixture was heated to 65° C. for 1.5 hours to 2 hours, and then cooled to 25° C.

The Grignard solution thus formed was added drop-wise, in about 2.5 hours to 3 hours, into a solution of dimethyl oxalate (54.3 g, 0.46 mol) dissolved in 300 mL of tetrahydrofuran, while maintaining the temperature at maximum 5-10° C. via cooling bath.

The solution was kept under stirring for 0.5 hours to 1.0 hours at 5-10° C., and then saturated ammonium chloride (1400 mL of a mixture of 650 g solid ammonium chloride and 2000 mL water) was added at 0° C., while monitoring the temperature (maximum 15-20° C.). Then, 150 mL of water and 625 mL of toluene were added. The separated organic phase was washed with water (900 mL), and then with brine (900 mL).

To the organic phase 7.5 g of charcoal was added, and the mixture was heated to 40° C. and stirred at this temperature for one hour.

The mixture was then filtered on decalite pad, and washed three times with toluene (3×150 mL)

This solution was concentrated at 50-55° C. under vacuum (about 30 mmHg) to 270 mL, heated to 65° C., and then 720 mL n-heptane was added drop-wise over 2.5 hours.

The solution was stirred for one hour at 65° C., and then cooled in 3 hours to 25° C. (about 1° C./5 min). It was then left stirring at this temperature for at least 8 hours, filtered on GochP3, and washed once with 150 mL n-heptane.

The creamy solid obtained was dried under vacuum at 45° C. for 7 hours yielding 73.6 g (63% overall yield, HPLC purity 99.8 area %).

Example 3

Crystallization of Methyl di-(2-thienyl)glycolate in Ethanol 96%/n-heptane

Crude methyl di-(2-thienyl)glycolate (2.0 g) was dissolved in ethanol 96% (8.0 ml) at 45° C. 16.0 mL of n-heptane were then added drop-wise at 45° C. in 20 minutes. The solution was maintained at 45° C. for hour, and then it was cooled to 0° C. in 1 hour, and left at this temperature for another hour. The solid was filtered on a sintered glass funnel and it was washed once with n-heptane (2 mL). Drying for 6 hours at 50° C. under vacuum yielded 1.4 g of methyl di-(2-thienyl)glycolate (70%)

Example 4

Crystallization of Methyl Di-(2-thienyl)glycolate in Absolute Ethanol/n-heptane

Crude methyl di-(2-thienyl)glycolate (10.0 g) was dissolved in absolute ethanol (30.0 mL) at 55° C. 80.0 mL of n-heptane was then added drop-wise at 55° C. in 30 minutes. The solution was maintained at 55° C. for 1 hour, and then it was cooled to room temperature over 3 hours, and left at this temperature for 6 hours. The solid was filtered on a sintered glass funnel and it was washed once with n-heptane (10.0 mL). Drying for 18 hours at 50° C. under vacuum yielded 8.0 g of Methyl di-(2-thienyl)glycolate (80%).

Example 5

Crystallization of Methyl Di-(2-thienyl)glycolate in Isopropanol/n-heptane

Crude methyl di-(2-thienyl)glycolate (5.0 g) was dissolved in isopropanol (20.0 mL) at 60° C. 40.0 mL of n-heptane was then added drop-wise at 60° C. in 30 minutes. The solution was maintained at 45° C. for 1 hour, and then it was cooled to 0° C. in 1 hour, and left at this temperature for another hour. The solid was filtered on a sintered glass funnel, and it was washed once with n-heptane (5.0 ml). Drying for 12 hours at 50° C. under vacuum yielded 3.6 g of methyl di-(2-thienyl) glycolate (72%).

Example 6

Crystallization of Methyl Di-(2-thienyl)glycolate in Toluene/n-heptane

Crude methyl di-(2-thienyl)glycolate (250.0 g) was dissolved in toluene (500 mL) at 55° C. 1750 mL of n-heptane was then added drop-wise at 55° C. in 2.5 hours. The solution was maintained at 55° C. for 1 hour, and then it was left to cool to room temperature over 16 hours, and then cooled to 0° C., and left at this temperature for 2 hours. The solid was filtered on a sintered glass funnel and it was washed twice with n-heptane (2×150 mL). Drying for 16 hours at 50° C. under vacuum yielded 184.1 of methyl di-(2-thienyl)glycolate (73.6%)

Example 7

Preparation of Scopine Hydrobromide in Ethanol 96%

100 g (0.228 mol) of scopolamine hydrobromide trihydrate was suspended in 1000 mL of ethanol 96%, and cooled to 0° C. Well ground sodium borohydride (30.23 g, 0.80 mol) was then added portion-wise, while maintaining the temperature at maximum 25-30° C., gas evolution was noticed.

The reaction mixture was left stirring at room temperature for 16 hours, and then filtered on decalite pad, and washed twice with 100 mL of ethanol 96%. Water (19 mL) was added to the filtered solution, it was left stirring for 1.5 hours, and the obtained white suspension was concentrated under vacuum (about 30 mmHg) at maximum 55° C. to give a residue of 300 mL. After 30 minutes at room temperature, the residue was filtered on GochP3, and washed twice with 50 mL of ethanol 96%.

The solution was then cooled to 0° C., and acidified with 30 mL hydrobromic acid 48% to a pH of 1. 700 mL tetrahydrofuran was added drop-wise, in 3 hours, to the reaction mixture at 0° C., and it was maintained at 0° C. for 5 hours. The white solid was then filtered on Goch P3, washed with 100 mL tetrahydrofuran, and dried at 50° C. under vacuum for 16 hours, yielding 33.2 g (64% yield, sulphuric ashes 0.7%).

Example 8

Preparation of Scopine Hydrobromide in Abs.ethanol with Precipitation in HBr 48%

5 g (11.4 mmol) of scopolamine hydrobromide trihydrate was suspended in 50 mL of absolute ethanol, and cooled to 0° C. Well ground sodium borohydride (1.73 g, 45.7 mmol) was then added portion-wise while maintaining the temperature at a maximum of 30° C.

4.0 ml water was then added to the reaction mixture, and then after 30 minutes, the suspension was filtered on decalite pad, and washed with 30 mL of absolute ethanol.

The obtained solution was concentrated under vacuum at 40° C. to residual 15 mL and, after 2 hours at room temperature, filtered on GochP3, and washed with 4 mL of absolute ethanol.

The solution was then cooled to 0° C., and acidified with hydrobromic acid 48% in water to obtain a pH of 1.

15 mL tetrahydrofuran was then added drop-wise to the reaction mixture at 0° C., and it was maintained at 0° C. for 2 hours and then at room temperature for 2 days. The white solid was filtered on Goch P3, and dried at 50° C. under vacuum for 16 hours, yielding 1.4 g (52%). The other 40 mL THF ("tetrahydrofuran") added to the mother liquor at 0° C. led to obtain other 700 mg product, containing 0.72% of salts.

Example 9

Preparation of Scopine Hydrobromide in Abs.ethanol (5-vol) with Precipitation in HBr 48%

10.0 g (22.84 mmol) of scopolamine hydrobromide trihydrate was suspended in 50 mL of absolute ethanol, and cooled to 0° C. Sodium borohydride (3.46 g, 68.6 mmol) was then added portion-wise while maintaining the temperature at a maximum of 30° C.

4.8 ml of water was then added to the reaction mixture, and after 30 minutes the suspension was filtered on decalite pad, and washed with 10 mL of absolute ethanol.

The solution was then cooled to 0° C., and acidified with hydrobromic acid 48% in water to obtain a pH of 1.

100 mL tetrahydrofuran was added drop-wise to the reaction mixture at 0° C., and it was maintained at 0° C. for 8 hours The white solid was filtered on Goch P3, and dried at 50° C. under vacuum for 16 hours, yielding 12.8 g (52%), containing 0.65% of salts.

Example 10

Preparation of Scopine Hydrobromide in Ethanol with Precipitation in HBr 48%

100 g (0.22 mol) of scopolamine hydrobromide trihydrate was suspended in 1000 mL of ethanol 1 96% and cooled to 0° C. Well ground sodium borohydride (30.23 g, 0.80 mol) was then added portion-wise maintaining the temperature at maximum 25-30° C., gas evolution was noticed. The reaction mixture was left stirring at room temperature for 16 hours and then filtered on decalite pad, and washed twice with 100 mL of Ethanol 96%. 19 mL water was added to the filtered solution, and it was left stirring for 1.5 hours. The obtained white suspension was concentrated under vacuum (about 30 mmHg) at maximum 55° C. to residual 300 mL and, after 30 minutes at room temperature, filtered on GochGoch P3 and washed twice with 50 mL of Ethanol 96%. The solution was then cooled to 0° C. and acidified with 30 mL hydrobromic acid 48% to a pH of 1. 1000 mL tetrahydrofuran was added drop-wise to the reaction mixture at 0° C. in 3 hours and maintained at 0° C. for 4-5 hours. The white solid was then filtered on Goch P3, washed with 100 mL tetrahydrofuran and dried at 50° C. under vacuum for 16 hours, yielding 45.9 g (85.6% yield, sulphuric ashes 12.7%).

Example 11

Preparation of N-dDemethyl-tiotropium 15 g (0.064 mol) of scopine hydrobromide was suspended in 165 mL of dimethylformamide at 25° C., then 17.6 g (0.127 mol) of anhydrous potassium carbonate were added, and the mixture was stirred at room temperature for about 60 minutes. 16.2 g (0.064 mol) of methyl di-(2-thienyl)glycolate were dissolved in 30 mL of dimethylformamide, and, with 4.4 g (0.032 mol) of anhydrous potassium carbonate, they were added to the reaction mixture at about 60-65° C. The suspension was heated to 65° C., under vacuum (70-100 mbar), and under nitrogen stripping (2.2-2.4 L/min) for 18 hours. At the end of the reaction the distilled DMF ("dimethylformamide") was reintroduced to the reaction mixture and another 2 volumes of DMF, for a total of 15 volumes (225 mL), were added. The reaction mixture was cooled to 0° C., and acidified to pH 3 with about 168 mL of 2M HBr (the temperature during the addition below 20° C.). The obtained solution was extracted twice with mL toluene, and the combined aqueous phases were then cooled to 0-5° C., and basified with 8.5 g of solid potassium carbonate to a pH of 9. After one hour at 0° C. the solid was filtered on Goch P3, and washed five times with 60 mL of water to obtain a pH of 7. The solid was dried under vacuum at 45° C. for 16 hours yielding 16.5 g (69% yield, 98.3% HPLC purity)

Example 12

Preparation of N-demethyl-tiotropium with a Scopine Containing High Percent of Salts 3.0 g (0.012 mol) of scopine hydrobromide containing 69% inorganic salts was suspended at room temperature in 27 mL of dimethylformamide, then 3.4 g (0.025 mol) of anhydrous potassium carbonate were added, and the mixture was stirred at room temperature for about 60 minutes. 3.1 g (0.012 mol) of methyl di-(2-thienyl)glycolate were dissolved in 9 mL of dimethylformamide, and, with 0.85 g (0.006 mol) of anhydrous potassium carbonate, they were added to the reaction mixture at about 60-65° C. The suspension was heated to 65° C., under vacuum (70-100 mbar), and under nitrogen stripping (2.2-2.4 L/min) for 18 hours. At the end of the reaction, the distilled DMF was re-added to the reaction mixture and other 2 volumes of DMF, for a total of 15 volumes (45 mL), were added. The reaction mixture was cooled to 0° C., and acidified to pH 3 with 33 mL of HBr 2M (temperature during addition below 20° C.) The obtained solution was extracted twice with 15 mL toluene, and the combined aqueous phases were then cooled to 0-5° C., and basified with 7.1 g of solid potassium carbonate to a pH of 9. After one hour at 0° C., the solid was filtered on Goch P3, and washed five times with 30 mL of water to obtain a pH of 7. The solid was dried under vacuum at 45° C. for 16 hours yielding 1.8 g (37.5% yield, 70% HPLC purity).

Example 13

Preparation of N-demethyl-tiotropium from Scopine Base and a Weak Inorganic Base 5.45 g (0.023 mol) of scopine hydrobromide was suspended in 30 mL of DCM, and then 5 g (0.036 mol) of potassium carbonate was added. The reaction mixture was stirred at room temperature for one hour and then filtered on Goch P3 and washed with acetonitrile several times, (using about 10 ml of acetonitrile). After evaporation of the filtered solution, 2.78 g of scopine base was obtained (77.5% yield). 3.0 g (0.02 mol) of scopine base was suspended at room temperature in 27 mL of dimethylformamide, then 2.7 g (0.02 mol) of anhydrous potassium carbonate was added, and the mixture was stirred at room temperature for about 60 minutes. 4.9 g (0.02 mol) of methyl di-(2-thienyl)glycolate were dissolved in 9 mL of dimethylformamide, and, with 1.33 g (0.0096 mol) of anhydrous potassium carbonate, they were added to the reaction mixture at about 60-65° C. The suspension was heated to 65° C., under vacuum (70-100 mbar), and under nitrogen stripping (2.2-2.4 L/min) for 18 hours. At the end of the reaction the distilled DMF was re-added to the reaction mixture and other 2 volumes of DMF, for a total of 15 volumes (45 mL), were added. The reaction mixture was cooled to 0° C., and acidified to a pH of 3 with 33 mL of 2M HBr (temperature during addition below 20° C.). The obtained solution was extracted twice with 15 mL toluene, and the combined aqueous phases were then cooled to 0-5° C., and basified with 7.1 g of solid potassium carbonate to a pH of 9. After one hour at 0° C., the solid was filtered on Goch P3, and washed five times with 30 mL of water to obtain a pH of 7. The solid was dried under vacuum at 45° C. for 16 hours yielding 5.1 g (69.5% yield, 98.5% HPLC purity)

Example 14

Preparation of Tiotropium Bromide 0.5 g of N-demethyl tiotropium (1.33 mmol) was suspended in a flask under nitrogen with 5 mL of CH$_3$CN. 0.525 g of CH$_3$Br 48% w/w solution in CH$_3$CN (0.00266 mol) was loaded and the suspension was left under stirring at 22° C. for 20 hours. The product was filtered and washed with 1 mL of CH$_3$CN. 375 mg of Tiotropium was obtained (HPLC purity 92.21%, starting material 7.68%).

Example 15

Preparation of Tiotropium Bromide 0.52 g of N-demethyl tiotropium (1.39 mmol) was suspended in a flask under nitrogen with 5.23 g of CH$_3$CN. 1.35 g of CH$_3$Br 50% w/w solution in CH$_3$CN (0.0071 mol) was loaded, and the suspension was left under stirring at 22° C. for 12 hours. The product was filtered and washed with 1 mL of CH$_3$CN. 572 mg of wet Tiotropium was obtained (HPLC purity 99.89%, starting material 0.07%).

Example 16

Preparation of Tiotropium Bromide 4.96 g of N-demethyl tiotropium (13.2 mmol) were loaded in a flask under nitrogen with 49.6 mL of CH$_3$CN. A suspension was obtained. 12.61 g of CH$_3$Br 50% w/w —CH$_3$CN solution—(0.066 mol) were loaded. The suspension was left under stirring at 22° C. for 64 hours. The product was filtered and washed with 2 mL of CH$_3$CN. 6.93 g of wet Tiotropium was obtained, and dried under vacuum at 45° C. for 22 h (residual pressure 4 mbar). 5.9 g of dry product (purity 99.8%, start 0.107%) was obtained.

Example 17

Crystallization of Tiotropium Bromide

Crude Tiotropium bromide (1.00 g) was dissolved in absolute ethanol (65 mL) at 78° C. The solution was heated to 78° C. for about 30 min, and then was cooled to 22° C. in at least 6 hours. The obtained suspension was maintained at 22° C. for at least 3 hours, and then was filtered on a sintered glass funnel, and the solid was washed twice with absolute ethanol (2×1.0 mL). The solid was dried for 30 min. at 22° C. under N$_2$ flow, and then for 9 hours at 60° C. under reduced pressure (17 mbar). 0.66 g of Tiotropium bromide was obtained.

Example 18

Preparation of Tiotropium Bromide Monohydrate from Tiotropium Bromide Ethanolate 13.45 g of dry Tiotropium bromide from example 16 was suspended in 80.7 mL of water and the suspension was stirred at room temperature for 4 h. After it was filtered washing with 10 mL of water was conducted. The product was left on the filter under vacuum and under nitrogen at room temperature for 15 min. 11.66 g of monohydrate was obtained. The content of water on the sample was 4.3% (TGA analysis).

Example 19

Comparative Preparation of Tiotropium Bromide from N-demethyl Tiotropium According to U.S. Pat. No. 5,610,163

10.0 g (0.0265 mole) of scopine di-(2-thienyl)glycolate was dissolved in a mixture comprising 20 mL of anhydrous methylene chloride and 30 mL of anhydrous acetonitrile and treated with 12.8 g (0.1325 mole) of methyl bromide (as 50% strength solution in anhydrous acetonitrile), and the reaction mixture was allowed to stand for 24 hours at room temperature in a tightly sealed reaction vessel. Crystals were precipitated during this time. They are filtered off under suction, washed using methylene chloride and dried at 35° C.—under reduced pressure. White crystals were obtained (from methanol/acetone), m.p. 217.8 C. (decomposition) after drying at 111° C. under reduced pressure.

Example 20

Preparation of Scopine Hydrochloride in Absolute Ethanol (5 vol) with Precipitation in HCl 37%

10.0 g (22.84 mmol) of scopolamine hydrobromide trihydrate was suspended in 50 mL of absolute ethanol, and cooled to 0° C. Sodium borohydride (3.46 g, 68.6 mmol) was then added portion-wise while maintaining the temperature at a maximum of 30° C.

4.8 mL of water was then added to the reaction mixture, and after 30 minutes the suspension was filtered on decalite pad, and washed with 10 mL of absolute ethanol.

The solution was then cooled to 0° C., and acidified with hydrochloric acid 37% in water to obtain a pH of 1.

100 mL of tetrahydrofuran was added drop-wise to the reaction mixture at 0° C., and it was maintained at 0° C. for 8 hours The white solid was filtered on Goch P3, and dried at 50° C. under vacuum for 16 hours, yielding 12.8 g (52%).

Example 21

Preparation of N-demethyl-tiotropium 13.2 g (0.064 mol) of scopine hydrochloride was suspended in 165 mL of dimethylformamide at 25° C., then 17.6 g (0.127 mol) of anhydrous potassium carbonate were added, and the mixture was stirred at room temperature for about 60 minutes. 16.2 g (0.064 mol) of methyl di-(2-thienyl)glycolate was dissolved in 30 mL of dimethylformamide, and with 4.4 g 0.032 mol) of anhydrous potassium carbonate, they were added to the reaction mixture at about 60-65° C. The suspension was heated to 65° C., under vacuum (70-100 mbar), and under nitrogen stripped (2.2-2.4 L/min) for 18 hours.

At the end of the reaction, the distilled DMF was re-introduced to the reaction mixture and the other 2 volumes of DMF, for a total of 15 volumes (225 mL), were added. The reaction mixture was cooled to 0° C., and acidified to a pH of 3 with about 168 mL of 2M HBr (temperature during addition was below 20° C.). The obtained solution was extracted twice with 85 mL of toluene, and the combined aqueous phases were then cooled to 0-5° C., and basified with 8.5 g of solid potassium carbonate to a pH of 9. After one hour at 0° C., the solid was filtered on Goch P3, and washed five times with 60 mL of water to obtain a pH of 7. The solid was dried under vacuum at 45° C. for 16 hours yielding 16.5 g (69% yield, 98.3% HPLC purity).

What is claimed is:

1. A process for preparing tiotropium bromide comprising:
a. preparing N-demethyl-tiotropium of formula III,

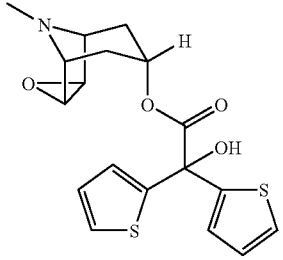

III comprising reacting methyl-di-(2-thienyl)-glycolate of formula I,

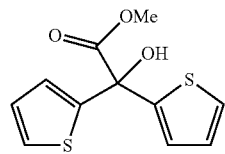

I with a scopine salt of formula II-s

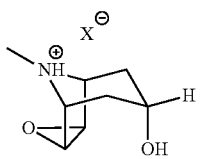

Formula II-s having an inorganic salt content of about 0.5% to about 40% (w/w) of the total weight, wherein X is selected from the group consisting of Br, Cl, $SO_4$, MeCOO, $PO_4$, $MeSO_3$, tartrate, fumarate, citrate, maleate, succinate, p-toluene sulphonate and amidosulphonate; and b. reacting said N-demethyl-tiotropium with methylbromide in an organic solvent to form tiotropium bromide.

2. The process of claim 1, wherein said organic solvent is selected from the group consisting of a $C_{2-4}$ nitrile, a $C_{4-8}$ linear or cyclic ether, a mixture of a $C_{2-4}$ nitrile and a $C_{4-8}$ linear or cyclic ether, a mixture of a $C_{7-8}$ aromatic hydrocarbon and a $C_{2-4}$ nitrile, and a mixture of a $C_{2-4}$ nitrile and a $C_{3-10}$ ketone.

3. The process of claim 2, wherein said organic solvent is selected from the group consisting of acetonitrile, tetrahydrofuran, a mixture of acetonitrile and tetrahydrofuran, a mixture of toluene and acetonitrile, and a mixture of acetone and acetonitrile.

4. The process of claim 3, wherein said organic solvent is acetonitrile.

* * * * *